United States Patent [19]

Fukushi

[11] Patent Number: 4,612,304
[45] Date of Patent: Sep. 16, 1986

[54] ANTITUMOR FORMULATION CONTAINING LIPOPOLYSACCHARIDE WITH TREHALOSE DERIVATIVES

[75] Inventor: Kazue Fukushi, Hirosaki, Japan

[73] Assignee: SS Pharmaceutical Co., Ltd., Tokyo, Japan

[21] Appl. No.: 743,613

[22] Filed: Jun. 11, 1985

[51] Int. Cl.$^4$ ............................................. A61K 31/715
[52] U.S. Cl. ...................................... 514/53; 514/54; 536/1.1; 536/119; 536/115
[58] Field of Search ..................... 536/119, 18.2, 115; 514/53, 54

[56] References Cited

U.S. PATENT DOCUMENTS

| | | | |
|---|---|---|---|
| 4,307,229 | 12/1981 | Liav et al. | 536/115 |
| 4,394,502 | 7/1983 | Maruyama | 536/119 |
| 4,454,119 | 6/1984 | Fukushi | 514/53 |

FOREIGN PATENT DOCUMENTS 0181297 10/1984 Japan ................... 536/119

OTHER PUBLICATIONS

Gensler et al., "Chem. Abst.", vol. 94, 1981, p. 76715y.
Nishikawa et al, "Chem. Abst.", vol. 101, 1984, p. 111340j.

*Primary Examiner*—Johnnie R. Brown
*Attorney, Agent, or Firm*—Oblon, Fisher, Spivak, McClelland & Maier

[57] ABSTRACT

Disclosed herein is an antitumor formulation, which contains an α,α-trehalose-6,6'-dicarboxylate, which is represented by the following general formula (I):

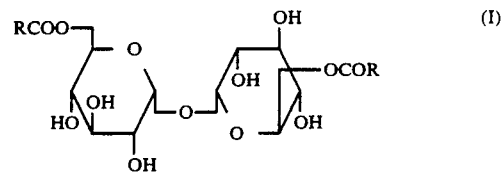

wherein R means a $C_1$–$C_{21}$ alkyl group, and a lipopolysaccharide. The antitumor formulation features low toxicity and high antitumor activities.

5 Claims, No Drawings

ANTITUMOR FORMULATION CONTAINING LIPOPOLYSACCHARIDE WITH TREHALOSE DERIVATIVES

BACKGROUND OF THE INVENTION

1. Field of the Invention:

This invention relates to an antitumor formulation, and more specifically to an antitumor formulation containing an α,α-trehalose-6,6'-dicarboxylate and a lipopolysaccharide.

2. Description of the Prior Art:

A variety of antitumor formulations have been developed to date. As one of such antitumor formulations, an antitumor formulation containing, in combination, a natural cord factor and a lipopolysaccharide either as is or in a form attenuated its toxicity by a treatment with an alkali (may hereinafter be abbreviated as "LPS") has been known (U.S. Pat. No. 4,454,119).

Since a natural cord factor can be obtained from BCG cells or the like through cumbersome treatments or processing, it has been accompanied by such drawbacks that its yield is low and its production cost is thus high and it is by itself a mixture of many analogues and it cannot hence be obtained with certain constant quality.

SUMMARY OF THE INVENTION

The present inventor has carried out an extensive research with a view toward obtaining a substance which can be advantageously prepared by a chemical process and when combined with LPS, exhibits antitumor activities superior to those of natural cord factors. As a result, it has been found that an α,α-trehalose-6,6'-dicarboxylate, which is represented by the following general formula (I):

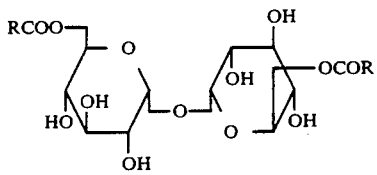

wherein R means a $C_1$–$C_{21}$ alkyl group, can meet the above-described requirements, leading to completion of this invention.

Accordingly, this invention provides an antitumor formulation comprising the α,α-trehalose-6,6'-dicarboxylate (I) and LPS. The antitumor formulation of this invention features low toxicity and high antitumor activities.

DETAILED DESCRIPTION OF THE INVENTION

The α,α-trehalose-6,6'-dicarboxylate (I) useful in the practice of this invention can be prepared in accordance with the process described in Japanese Patent Laid-open No. 185,599/1983, namely, in the following manner:

Trehalose ⟶ (I)

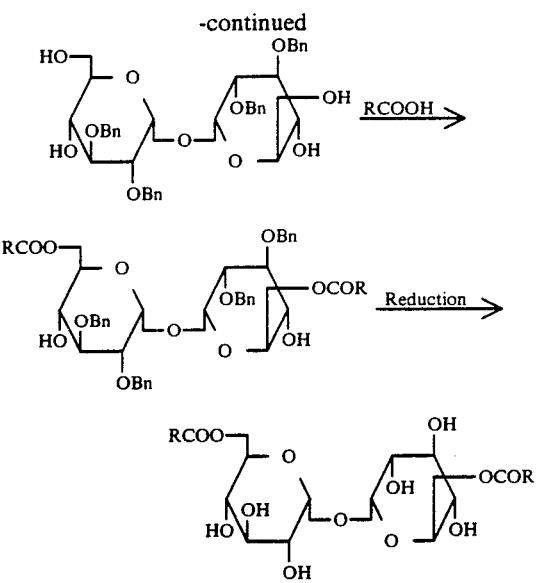

wherein R has the same meaning as defined above and Bn denotes a benzyl group.

The followings are physiochemical properties of certain representative compounds of the α,α-trehalose-6,6'-dicarboxylates (I).

| Comp'd | R ($C_nH_{2n+1}$) | m.p.(°C.) | $[\alpha]_{D(chloroform)}^{20C=1.0}$ | $IR\nu_{max}^{KBr}cm^{-1}$ |
|---|---|---|---|---|
| 1 | n = 1 | 151–154 | +168.0 | 1740 |
| 2 | n = 7 | 170–171 | +116.6 | 1735 |
| 3 | n = 9 | 159–163 | +108.8 | 1740 |
| 4 | n = 11 | 161–164 | +88.4 | 1730 |
| 5 | n = 13 | 157–161 | +82.8 | 1730 |
| 6 | n = 15 | 160–162 | +75.3 | 1730 |
| 7 | n = 17 | 157–160 | +80.8 | 1735 |
| 8 | n = 21 | 129–134 | +65.6 | 1735 |

Incidentally, as particularly preferred compounds of the α,α-trehalose-6,6'-dicarboxylates (I), may for example be mentioned those containing heptyl, nonyl, undecyl, dodecyl and the like as the alkyl groups indicated by Rs in the general formula (I).

On the other hand, LPSs are obtained in a below-described manner from gram-negative bacilli such as Escherichia, Salmonella, Pseudomonas, Serratia, Shigella, Proteus, Brucella, Enterobactor, Klebsiella, Vibrio and the like or their mutants. Of these LPSs, those obtained respectively from *S. minnesota*, *S. typhimurium*, *S. marcescens* and *E. coli* are preferred owing to their low pathogenicity.

An LPS used in this invention may be obtained by subjecting either whole cells or cell walls of either one of the above-mentioned gram-negative bacilli to either one of (1) the phenol-water extraction method [Westphal et al., Z. Naturforschung, 73, 148(1952)], (2) the liquid phenol-chloroform-petroleum ether extraction method [Galanos, et al., Eur., J. Biochemistry, 9, 245-249(1969)] and (3) the chloroform-methanol extraction method [Chen et al., J. Infect. Dis., 128, 543-551(1973)]. If necessary or desirous, the LPS obtained in the above manner may further be attenuated prior to its use by subjecting it to a treatment with an alkali such as sodium hydroxide, hydroxylamine, ammonia, potassium hydroxide, alkaline hydroxylamine, hydrazine or the like. Such a treatment is effected usually at pH 8, at 20°–100° C., for 30 seconds to several days or preferably 1 minute to 1 hour. The time required for this treatment may be shortened as the pH level or temperature increases.

The antitumor formulation of this invention may be prepared by incorporating and forming the thus-obtained α,α-trehalose-6,6'-dicarboxylate (I) and LPS into a dosable preparation in a manner known commonly in the art. The mixing ratio of the compound (I) to the LPS may range from 10:1 to 1:10 with the range of from 2:1 to 1:4 being particularly preferred. The antitumor formulation of this invention may be applied, as an injectable solution, by intratumor administration subcutaneous administration, intramuscular administration or intravascular administration, or alternatively as a mixture with a transfusional solution or the like. Depending on the manner of its application or administration, it is feasible to employ additional ingredients known conventionally in the art, for example, an isotonic agent such as sodium chloride, dispersant such as polyvinylpyrrolidone, oil or fat such as mineral or vegetable oil or fat, emulsifier such as lecithin or surfactant, pH regulator such as carbonate or phosphate and/or the like.

It is preferred to either increase or decrease the dose of the thus-obtained antitumor formulation of this invention in accordance with the symptom of each patient. It may usually be administered at 0.01–100 mg/Kg/day or so.

By the way, natural cord factors are practically non-toxic to rats and guinea pigs but they give fatal toxicity to mice even at extremely trace levels, as known for many years [*J. Med. Chem.*, 23, 819(1980), etc.]. However, almost no cases of death were observed when the α,α-trehalose-6,6'-dicarboxylates of this invention were administered to ICR mice even at such a high dose of 150 mg/Kg (i.p.) ×5. On the other hand, the $LD_{50}$ of an LPS for male mice is 100 mg/Kg or more. This toxicity level can also be reduced to from one several tenth to one several hundredth by its toxicity attenuation. It is thus clear that the antitumor formulation of this invention, which contains the α,α-trehalose-6,6'-dicarboxylate (I) and LPS in combination, has lower toxicity than those making the combined use of natural cord factors and LPSs.

[Examples]

This invention will hereinafter be described by the following Examples and Referential Examples.

REFERENTIAL EXAMPLE 1

Twenty milliliters of pyridine and 20 ml of dichloromethane were added to 2.0 g of 2,3,2',3'-tetra-o-benzyl-α,α-trehalose to dissolve the latter. While stirring the resultant solution at 0° C. with ice-cooling, 1.8 g of stearoyl chloride was added dropwise. After stirring the resultant mixture for 30 minutes, it was stirred at room temperature for further 1 hour. The reaction mixture was poured into ice water, followed by its extraction with chloroform. The chloroform was distilled off under reduced pressure, and the residue was then purified by silica gel column chromatography to obtain 2.9 g of 2,3,2',3'-tetra-o-benzyl-6,6'-di-o-stearoyl-α,α-trehalose as a colorless waxy matter. Yield: 83%.

$[\alpha]_D^{20}$: +58.8° (C=1.0, chloroform).

IR $\nu_{max}^{KBr}$cm$^{-1}$: 1740 (>C=O)

NMR (60 MHz, d$_1$-chloroform) δppm: 0.88(t, 6H, J=5Hz), 1.23(m, 60H), 2.0–2.5(m, 4H), 3.3–4.3(m, 12H), 5.14(d, 2H, J=3.5Hz), 4.66(s, 4H), 4.86(d, 4H), 7.0–7.4(m, 20H).

REFERENTIAL EXAMPLE 2

Added to 1.24 g of 2,3,2',3'-tetra-o-benzyl-6,6'-di-o-stearoyl-α,α-trehalose was 20 ml of chloroform to dissolve the former, followed by an addition of 0.5 g of palladium black as a catalyst. Hydrogen gas was introduced to catalytically reduce the trehalose derivative for 1 hour. The liquid reaction mixture was filtered to remove the catalyst and the filtrate was concentrated to dryness under reduced pressure. The residue was recrystallized from sopropanol to obtain 0.55 g of 6,6'-di-o-stearoyl-α,α-trehalose as colorless acicular crystals. Yield: 63%.

m.p.: 157–160° C.

$[\alpha]_D^{20}$: +80.8°(C=1.0, chloroform).

IR $\nu_{max}^{KBr}$cm$^{-1}$: 1735 (>C=O)

NMR (100 MHz, d$_5$-pyridine) δppm: 0.88(t, 6H, J=6.5Hz), 1.1–1.8(m, 60H), 2.2–2.4(t, 4H, J=7Hz), 4.0–2.5(m, 4H), 4.5–5.2(m, 8H), 5.84 (d, 2H, J=3.5Hz).

REFERENTIAL EXAMPLE 3

Extraction of LPS (by the PCP method)

Fifty grams of ethanol-acetone-ether dried whole cells of *S. minnesota* 1167-R 595 (Re) (FERM BP-13) were suspended in 200 ml of a PCP solvent (liquid phenol:chloroform:petroleum ether =2:5:8), followed by homogenization of the resultant suspension at 5°–20° C. for 5 minutes. It was then centrifuged at 5,000 rpm for 15 minutes into a supernatant and a residue of the cell bodies. The residue was extracted twice with the PCP solvent. The thus-obtained extracts were combined with the supernatant. Using a rotary evaporator (30° C. –40° C.), the chloroform and petroleum ether were distilled off from the solution. Water was added to the residue to cause glycolipids to precipitate. The precipitate was collected by filtration and washed 2-3 times with about 5 ml of 80% phenol. Ether was thereafter added to remove the phenol. The residue was then dried under reduced pressure, to which 50 ml of distilled water was added. The resultant mixture was heated at about 45° C. to dissolve the residue. The thus-obtained mixture was centrifuged at 100,000×g for 4 hours to obtain a transparent pellet. It was thereafter lyophilized to obtain 1.5 g of an LPS.

REFERENTIAL EXAMPLE 4

Attenuation of Toxicity of the LPS:

(i) The LPS obtained in Referential Example 3 was treated and attenuated at 37° C. for 30 minutes in a 0.1 N solution of sodium hydroxide in ethanol.

(ii) The LPS obtained in Referential Example 3 was treated for 3 minutes in a 2% solution of alkaline (NaOH) hydroxylamine in ethanol. After neutralizing with hydrochloric acid, the thus-treated LPS was lyophilized. Chloroform was added to the lyophilized LPS, and the insoluble matter was dissolved in water and lyophilized again to obtain the LPS in an attenuated form.

EXAMPLE 1

Line 10 hepatoma cells which had been induced by diethylnitrosamine and then maintained in ascitics form were intradermally inoculated at a rate of 1×10$^6$ cells per head to lateroabdomen of inbred Strain-2 guinea pigs (body weight: 300–400 g). Seven days after the injection, the formation of tumors was observed. Then, each sample drug was injected in an amount of 0.4 ml into one of the tumors. Ninety days later, the number of cured guinea pigs was counted to calculate the percent cure. As sample drugs, were used formulations obtained each by homogenizing 200 μg of α,α-trehalose-6,6-dioctanoate, a representative compound in the present invention, or 100 μg of a natural cord factor obtained from tubercle bacillus in a manner known per se in the art and 200 μg of an LPS obtained from S. minnesota Re mutant in 0.4 ml of a 0.15 M phosphate buffer of pH 7.4 which contained 1% of a mineral oil ("Violess U-6"; product of Maruzen Oil Co., Ltd.) and 0.2% of "Tween 80". Results are shown in the following table.

|  | Sample drug | Cured/tested | Percent cure (%) |
|---|---|---|---|
| Invention product | α,α-Trehalose-6,6'-dioctanoate + LPS | 9/10 | 90 |
| Comparative product | Natural cord factor + LPS | 6/10 | 60 |
|  | Control | 0/10 | 0 |

As shown in the above table, the combined use of the α,α-trehalose-6,6'-dicarboxylate and LPS in accordance with the present invention brought about significantly stronger antitumor activities compared with the combined use of the conventionally-known natural cord factor and LPS, and is extremely useful as an antitumor formulation.

EXAMPLE 2

Emulsified Formulation:

To 1 mg of α,α-trehalose-6,6'-didecanoate and 1 mg of LPS obtained from S. minnesota Re mutant, 100 mg of sesame oil and 5 mg of purified yolk lecithin were added. Water was added with stirring to the resultant mixture to emulsify the same. An emulsified formulation of 10 ml in total was obtained.

What is claimed is:

1. An antitumor formulation comprising an α,α-trehalose-6,6'-dicarboxylate, which is represented by the following general formula (I):

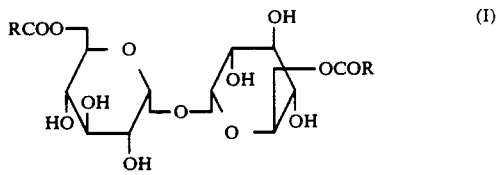

wherein R represents a $C_1$–$C_{21}$ alkyl group, and a lipopolysaccharide, the ratio of compound I to the lipopolysaccharide ranging from 10:1 to 1:10.

2. An antitumor formulation as claimed in claim 1, wherein the lipopolysaccharide is previously treated with alkali to attenuate its toxicity.

3. An antitumor formulation as claimed in claim 1, wherein the ratio ranges from 2:1 to 1:4.

4. An antitumor formulation as claimed in claim 1, wherein R represents a $C_8$–$C_{10}$ alkyl group.

5. An antitumor formulation as claimed in claim 4, wherein compound I is α,α-trehalose-6,6'-dioctanoate.

* * * * *